US006635081B2

(12) United States Patent
Khosravi et al.

(10) Patent No.: US 6,635,081 B2
(45) Date of Patent: *Oct. 21, 2003

(54) COILED-SHEET STENT-GRAFT WITH SLIDABLE EXO-SKELETON

(75) Inventors: Farhad Khosravi, San Mateo, CA (US); Himanshu N. Patel, San Jose, CA (US)

(73) Assignee: Endotex Interventional Systems, Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/996,473

(22) Filed: Nov. 27, 2001

(65) Prior Publication Data

US 2002/0038142 A1 Mar. 28, 2002

Related U.S. Application Data

(63) Continuation of application No. 09/288,866, filed on Apr. 9, 1999, now Pat. No. 6,322,585, which is a continuation-in-part of application No. 09/192,977, filed on Nov. 16, 1998, now Pat. No. 6,325,820.

(51) Int. Cl.[7] .................................................. A61F 2/06

(52) U.S. Cl. ...................................................... 623/1.13

(58) Field of Search ........................ 623/1.13, 1.11–1.14, 623/1.15, 1.35, 1.38, 1.18, 1.44, 1.23; 606/195, 108

(56) References Cited

U.S. PATENT DOCUMENTS

| | | |
|---|---|---|
| 5,122,154 A | 6/1992 | Rhodes |
| 5,151,105 A | 9/1992 | Kwan-Gett |
| 5,545,211 A | 8/1996 | An et al. |
| 5,578,071 A | 11/1996 | Parodi |
| 5,643,208 A | 7/1997 | Parodi |
| 5,649,977 A | 7/1997 | Campbell |
| 5,662,713 A | 9/1997 | Anderen et al. |
| 5,667,523 A | 9/1997 | Bynon et al. |
| 5,674,276 A | 10/1997 | Andersen et al. |
| 5,681,345 A | 10/1997 | Euteneuer |
| 5,723,003 A | 3/1998 | Winston et al. |

(List continued on next page.)

OTHER PUBLICATIONS

EPO Publication No. 0 464 755 A1, Yoshihiko Kubo, et al, "Artificial Tubular Organ", Jan. 8, 1992.
EPO Publication No. 0 686 379 A2, Thomas J. Fogerty, et al., "Apparatus for Endoluminal Graft Placement", Dec. 13, 1995.
PCT Publication No. WO 96/21404, Charles T. Maroney, "Kink–Resistant Stent–Graft", Jul. 18, 1996.
PCT Publication No. WO 98.11847, Mar. 28, 1998.

Primary Examiner—Michael J. Milano
Assistant Examiner—Tan-Uyen T. Ho
(74) Attorney, Agent, or Firm—Orrick, Herrington & Sutcliffe LLP

(57) ABSTRACT

A stent-graft having an exo-skeleton attached to a tubular graft, the tubular graft having a peripheral wall defining a lumen therein extending between first and second ends. One or more support elements, defining the exo-skeleton, are attached to the tubular graft, each support element extending generally peripherally around the tubular graft, each support element including generally axial segments and generally peripheral segments. A plurality of first fasteners attach the plurality of support elements to the wall of the tubular graft, at least one generally axial segment being slidably engaged by each first fastener. A plurality of second fasteners also attach the plurality of support elements to the wall of the tubular graft, each second fastener substantially anchoring a generally peripheral segment of the respective support element to the wall of the tubular graft. The stent-graft also includes first and second stents on the first and second ends for substantially anchoring the respective ends within a body passage.

23 Claims, 6 Drawing Sheets

U.S. PATENT DOCUMENTS

| | | |
|---|---|---|
| 5,723,004 A | 3/1998 | Dereume et al. |
| 5,725,549 A | 3/1998 | Lam |
| 5,728,131 A | 3/1998 | Frantzen et al. |
| 5,772,680 A | 6/1998 | Kieturakis et al. |
| 5,782,904 A | 7/1998 | White et al. |
| 5,800,526 A | 9/1998 | Anderson et al. |
| 5,817,126 A | 10/1998 | Imran |
| 5,824,040 A | 10/1998 | Cox et al. |
| 5,824,043 A | 10/1998 | Cottone, Jr. |
| 5,824,054 A | 10/1998 | Khosravi et al. |
| 5,843,164 A | 12/1998 | Frantzen et al. |
| 5,843,168 A | 12/1998 | Dang |
| 5,873,906 A | 2/1999 | Lau et al. |
| 5,916,264 A | 6/1999 | Von Oepen et al. |
| 5,925,076 A | 7/1999 | Inoue |
| 5,938,697 A | 8/1999 | Kahon |
| 5,976,182 A | 11/1999 | Cox |
| 5,980,563 A | 11/1999 | Tu et al. |
| 5,980,565 A | 11/1999 | Jayaraman |
| 5,989,280 A | 11/1999 | Euteneuer et al. |
| 6,004,348 A | 12/1999 | Banas et al. |
| 6,015,431 A | 1/2000 | Thornton et al. |
| 6,042,605 A | 3/2000 | Martin et al. |
| 6,071,307 A | 6/2000 | Rhee et al. |
| 6,322,585 B1 * | 11/2001 | Khosravi et al. .......... 632/1.11 |
| 6,325,820 B1 * | 12/2001 | Khosravi et al. .......... 623/1.13 |

* cited by examiner

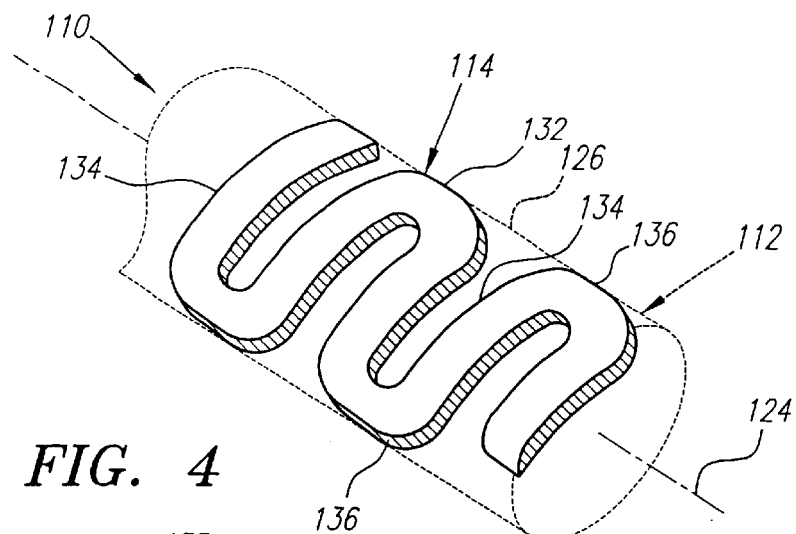
FIG. 4
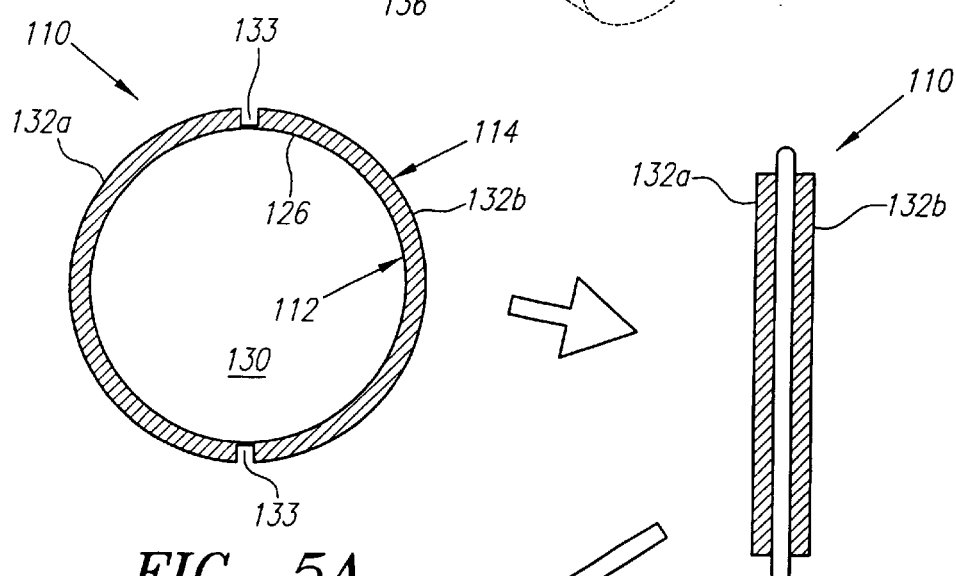
FIG. 5A
FIG. 5B
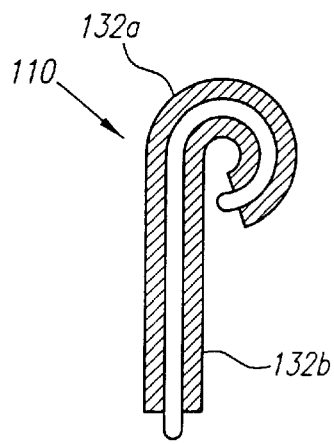
FIG. 5C
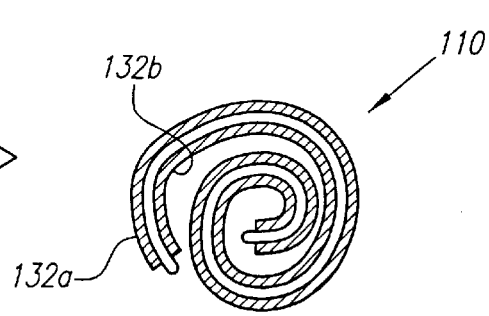
FIG. 5D

COILED-SHEET STENT-GRAFT WITH SLIDABLE EXO-SKELETON

This application is a Continuations co-pending application Ser. No. 09/288,866, filed Apr. 9, 1999, U.S. Pat. No. 6,322,585, which is a continuation-in-part of application Ser. No. 09/192,977, U.S. Pat. No. 6,325,820, filed Nov. 16, 1998, the disclosures of which are expressly incorporated herein by reference.

FIELD OF THE INVENTION

The present invention relates generally to prostheses for implantation with body lumens, and more particularly to a stent-graft having a flexible exo-skeleton slidably attached to a tubular graft.

BACKGROUND

Graft prostheses are often implanted within blood vessels, particularly the aorta or other arteries, which may be subject to aneurysm formation and/or severe atherosclerotic disease which may involve multiple stenoses. For example, an aortic aneurysm may develop in a patient, for example, within the abdominal aorta at the aorto-iliac bifurcation, requiring treatment before the vessel wall ruptures. To repair a blood vessel damaged by such an affliction, a procedure involving use of a graft prosthesis is generally performed.

A number of graft prostheses have been suggested that include a tubular graft attached to a stent. The tubular graft may be a biocompatible porous or nonporous tubular structure to which a stent structure, such as a wire mesh, may be attached. The stent structure may be biased to assume an enlarged configuration corresponding to a target treatment site, but may be constrained in a contracted condition to facilitate introduction into a patient's vasculature. The graft prosthesis may be percutaneously introduced in the contracted condition, advanced to a treatment site within a blood vessel, and released to assume the enlarged condition and repair and/or bypass the treatment site.

One problem often associated with such prostheses is effectively securing the tubular graft at the treatment site. The released graft prosthesis may not sufficiently engage the vessel wall adjacent the treatment site, possibly resulting in the graft prosthesis moving after implantation, which may expose the damaged vessel wall. Plastically deformable expandable stent structures may be provided to attempt to more directly control the engagement between the graft prosthesis and the vessel wall. Such plastically deformable structures, however, may not provide desired flexibility transverse to the longitudinal axis of the stent, making direction through and/or implantation within tortuous body passages difficult. Further, they also generally require the use of a balloon or other expandable member to expand the stent structure to the enlarged condition, which may introduce risks of uneven stent structure expansion and/or balloon rupture.

In addition to plastically deformable stents, coiled-sheet stent structures have been suggested. Coiled-sheet stents may provide enhanced anchoring within the blood vessel because the size of the fully expanded stent may be more precisely controlled. Coiled sheet stents may be substantially evenly expanded and generally do not involve plastic deformation of the stent material. A coiled-sheet stent, however, may be substantially rigid transverse to its longitudinal axis, potentially resulting in a less flexible graft prosthesis, which may not be implanted effectively in tortuous anatomical conditions.

Graft prostheses may also be vulnerable when subjected to longitudinal compression, which is often encountered after implantation. The vessel wall may at least partially recover after a graft has been implanted and the underlying vessel wall no longer experiences substantial blood pressure. If the vessel wall shortens longitudinally during recovery, it may cause the graft material to buckle and kink, thereby potentially constricting flow through the graft prosthesis.

Therefore, there is a need for an-improved stent-graft that may provide improved flexibility and/or graft support, while still providing substantial anchoring within a blood vessel.

SUMMARY OF THE INVENTION

The present invention is directed to a stent-graft having an exo-skeleton attached to a tubular graft. In accordance with one aspect of the present invention, a stent-graft is provided that includes a tubular graft having a peripheral wall defining a periphery and a lumen therein, the lumen extending axially between first and second ends of the tubular graft. An exo-skeleton is attached to the peripheral wall, the exo-skeleton including one or more serpentine elements, each serpentine element extending both peripherally, i.e., in a manner which generally surrounds the wall which may be circular, elliptical or other suitable configuration, and axially along at least a portion of the peripheral wall. A stent is provided on the first and/or second ends for substantially anchoring the ends within a body passage.

In a preferred form, each serpentine element is a zigzag structure extending peripherally about the peripheral wall of the tubular graft. More preferably, a plurality of serpentine elements are distributed axially along the peripheral wall for providing articulation of the tubular graft between adjacent serpentine elements. The serpentine elements may be individually attached to the peripheral wall and/or the serpentine elements may be connected to one another by one or more connector elements extending between adjacent serpentine elements.

In another preferred form, each serpentine element defines a generally sinusoidal shape extending axially along the peripheral wall. Preferably, a plurality of serpentine elements may distributed substantially evenly about the periphery of the peripheral wall. Each of these serpentine elements preferably includes substantially transverse peripheral elements, adjacent transverse peripheral elements being connected by alternating curved elements, thereby defining the generally sinusoidal shape.

The exo-skeleton of the stent-graft is preferably directable between a contracted condition for facilitating introduction within a body passage and an enlarged condition for deployment within the body passage. The exo-skeleton may substantially support the tubular graft to hold the lumen of the tubular graft substantially open in the enlarged condition. In a preferred form, the exo-skeleton is radially compressible to the contracted condition and biased to assume the enlarged condition. Alternatively, the contracted condition of the exo-skeleton may be achieved by flattening and circumferentially rolling the exo-skeleton.

The tubular graft may be provided from a polymeric material, such as polyester, polytetrafluorethaline, dacron, teflon, and polyurethane. The exo-skeleton may be attached to the tubular graft by sutures, staples, wires, or an adhesive, or alternatively by thermal bonding, chemical bonding, and ultrasonic bonding. The exo-skeleton may be formed from a metallic material, such as stainless steel or Nitinol, and may be a flat-coiled sheet with the one or more serpentine elements formed therein, or a wire formed into a serpentine shape.

In alternative forms, the first and second ends of the tubular graft may have similar cross-sections, or the first end of the tubular graft may have a cross-section that is substantially smaller than a cross-section of the second end of the tubular graft. In addition, the exo-skeleton may be attached to an exterior surface of the tubular graft, to an interior surface of the tubular graft, or embedded in the wall of the tubular graft.

In accordance with another aspect of the present invention, a stent-graft is provided for placement within a bifurcation that includes a first tubular graft segment having a first end and a second bifurcated end, the first tubular graft segment having a first peripheral wall. A second tubular graft segment extends from the second bifurcated end, the second tubular graft segment having a second peripheral wall. An exo-skeleton is attached to at least one of the first and second peripheral walls, the exo-skeleton including one or more serpentine elements, each serpentine element extending both peripherally and axially along at least a portion of the respective peripheral wall to which it is attached.

A coiled-sheet stent may be provided on the first end for substantially anchoring the first end within a body passage. Similarly, a coiled-sheet stent may be provided on the second tubular graft segment opposite the second end of the first tubular graft segment.

Preferably, the stent-graft also includes a third tubular graft segment attachable to the second bifurcated end, the third tubular graft segment having a third peripheral wall. The exo-skeleton also may include one or more serpentine elements attached to the third peripheral wall.

In accordance with still another aspect of the present invention, a stent-graft having a slidable exo-skeleton is provided. The stent graft includes a tubular graft having a wall defining a circumference or other periphery and a lumen therein, the lumen extending axially between first and second open ends of the tubular graft. One or more support elements are attached to the tubular graft, each support element extending generally peripherally around the tubular graft, each support element including generally axial segments and generally circumferential or peripheral segments. A plurality of first fasteners are provided for attaching the plurality of support elements to the wall of the tubular graft, at least one generally axial segment being slidably engaged by each first fastener. In addition, a plurality of second fasteners may also be provided for attaching the plurality of support elements to the wall of the tubular graft, each second fastener substantially anchoring a segment of the respective support element to the wall of the tubular graft. In a preferred form, the stent-graft also includes a first stent on the first end and/or a second stent on the second end for substantially anchoring the respective first and/or second ends within a body passage.

In one form, a set of first fasteners, such as sutures, staples or wires, is attached to respective first wall regions of the tubular graft, each first fastener slidably securing one or more axial segments therein, whereby the axial segments slidably secured by each first fastener may slide axially with respect to the respective first wall region. More preferably, each first fastener may slidably secure at least two axial segments of adjacent support elements to a respective wall region, whereby the two axial segments may independently slide axially with respect to the respective first wall region and/or with respect to each other. Preferably, a set of second fasteners is attached to respective second wall regions of the tubular graft, each second fastener substantially anchoring a peripheral segment to the respective second wall region.

Thus, a stent-graft in accordance with the present invention may have a substantially flexible region that may conform substantially to the anatomy of a treatment site. Preferably, the flexible region is defined by an exo-skeleton attached to a tubular graft that includes one or more serpentine elements. The serpentine elements may facilitate articulation between adjacent serpentine elements, and/or may be sufficiently resilient and flexible to allow articulation, compression and/or expansion of the serpentine elements themselves.

Preferably, the stent-graft also includes sealing members, preferably coiled-sheet stents, attached to the ends of the tubular graft for substantially sealing and/or anchoring the ends of the tubular graft proximate the treatment site. Thus, the stent-graft may accommodate tortuous anatomy while still providing effective sealing and anchoring within a body passage.

Other objects and features of the present invention will become apparent from consideration of the following description taken in conjunction with the accompanying drawings.

BRIEF DESCRIPTION OF THE DRAWINGS

FIG. 4 is a perspective view of an alternative embodiment of a serpentine element attachable to a tubular graft (in phantom).

FIGS. 5A–5D are end views of a stent-graft in accordance with the present invention, showing a method for rolling the stent-graft into a contracted condition.

DETAILED DESCRIPTION OF THE PREFERRED EMBODIMENTS

Figure 1:
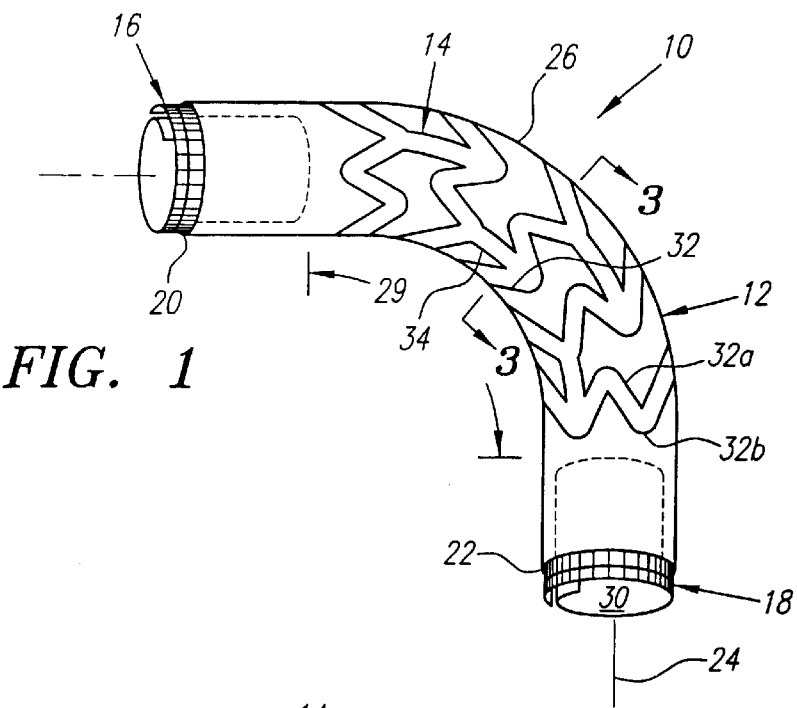
FIG. 1 shows a perspective view of a stent-graft with exo-skeleton in accordance with the present invention.

Turning now to the drawings, FIG. 1 shows a first preferred embodiment of a stent-graft 10 in accordance with the present invention that includes a tubular graft 12, an exo-skeleton 14, and first and second coiled-sheet stents 16, 18. The tubular graft 12 has first and second ends 20, 22 defining a longitudinal axis 24 therebetween and a peripheral wall 26 defining a periphery 28 and a lumen 30 therein. The tubular graft 12 may be formed from a variety of biocompatible materials, preferably a polymeric material, such as polyester, polytetrafluorethaline, dacron, teflon, and polyurethane.

The exo-skeleton 14 is attached to the peripheral wall 26 and includes a plurality of serpentine elements 32. The exo-skeleton 14 may be formed from a variety of semi-rigid materials, preferably a biocompatible metallic material, such as Nitinol or stainless steel. The material may be resiliently deformable, may exhibit shape memory properties and/or may be plastically deformable, as described further below, to facilitate articulation of the stent-graft 10, and/or the collapse and/or expansion of the exo-skeleton 14 between a contracted condition and an enlarged condition. The exo-skeleton 14 may be formed from flat sheet material having the individual serpentine elements 32 etched, cut or otherwise formed from the sheet material. Alternatively, the exo-skeleton 14 may be formed from wire-like materials, for example, by forming each serpentine element 32 from a single strand of wire.

The exo-skeleton 14 may be attached either to the exterior of the peripheral wall 26, to the interior of the peripheral wall 26, or alternatively embedded in the peripheral wall 26, with the term "exo-skeleton" being intended to include any of these locations and not to be limited to one location over another. The exo-skeleton 14 may be attached by mechanical fasteners, such as sutures, wires, staples, and the like, by an adhesive, or by a bonding process, such as thermal bonding, chemical bonding, or ultrasonic bonding.

Each serpentine element 32 extends both "peripherally" and "axially" along at least a portion of the peripheral wall 26. "Peripherally" refers to each serpentine element 32 extending in a manner which generally surrounds the peripheral wall 26 which preferably may be circular or elliptical, e.g., generally around the circumference or other periphery of the peripheral wall 26, while "axially" refers to the serpentine element 32 extending along the peripheral wall 26 generally parallel to the longitudinal axis 24. Thus, each serpentine element 32 defines a generally "zigzag" shape made up, for example, of abrupt "Z" and/or rounded "U" shaped elements integrally connected together.

Figure 2:
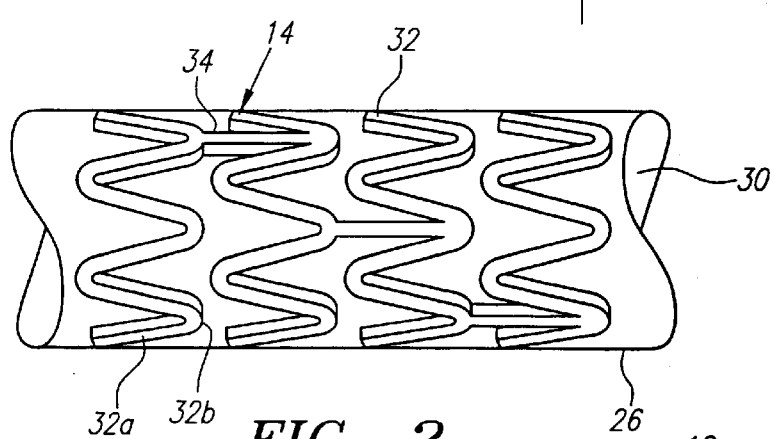
FIG. 2 is a side view detail of the stent-graft of FIG. 1, showing a first preferred embodiment of a plurality of serpentine elements defining the exo-skeleton.

In a first preferred form, shown in FIGS. 1 and 2, the serpentine elements 14 are defined by a plurality of zigzag elements, including generally straight axial regions 32a and alternating curved peripheral regions 32b, integrally formed together that extend substantially peripherally about the peripheral wall 26. The serpentine elements 32 consequently provide a multi-cellular exo-skeleton 14 that may facilitate articulation between adjacent serpentine elements 32 when the stent-graft 10 is directed substantially transversely with respect to the longitudinal axis 24.

In one form, the serpentine elements 32 are connected by connector elements 34, which preferably extend substantially axially between adjacent serpentine elements 32. The connector elements 34 may be formed, etched or cut when the serpentine elements are formed from a flat sheet, or the connector elements 34 may be strands of wire attached to the serpentine elements 32 in a conventional manner. Alternatively, the serpentine elements 32 may be separate structures that are individually attached to the peripheral wall 26 of the tubular graft 12.

The coiled-sheet stents 16, 18 may be attached to and extend partially from the respective ends 20, 22 of the tubular graft, preferably attached to the interior of the peripheral wall 26, although alternatively the coiled-sheet stents 16, 18 may be provided as separate components from the tubular graft 12. The coiled-sheet stents 16, 18 may at least partially expand automatically, but are preferably also mechanically expandable, e.g., they may be ratchetable to larger diameters, for example, using a balloon or other expandable member (not shown).

Figure 9:
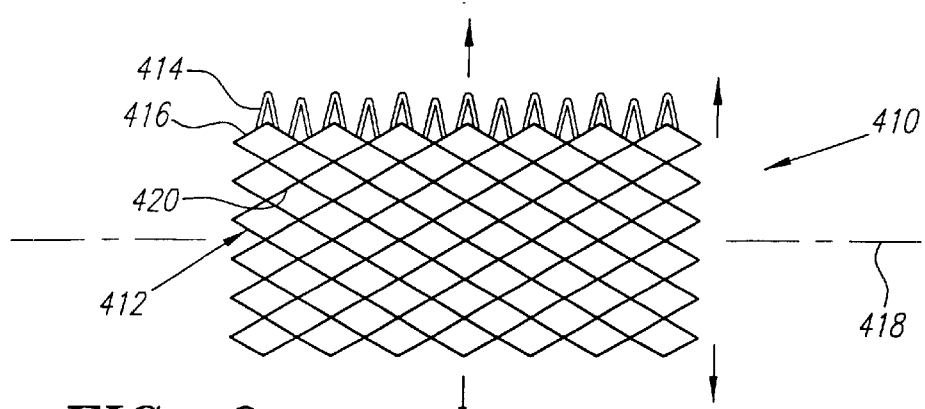
FIG. 9 is a side view of a fully stretchable stent for use with a stent-graft in accordance with the present invention.

The coiled-sheet stents 16, 18 may have a stretchable design, a stretchable anti-buckling segment, and/or a stretchable crowning end. For example, as shown in FIG. 9, a fully stretchable coiled-sheet stent 410 is shown that is formed from a substantially flat mesh structure 412 defining individual resilient mesh elements 420 and having teeth 414 along a side edge 416 thereof for being received within the mesh elements 420. The mesh structure 412 may be rolled or coiled to define a longitudinal axis 418 and a circumference or periphery (not shown) in a plane substantially perpendicular to the longitudinal axis 418. The mesh structure 412 may be formed from a plastically deformable material, such as stainless steel.

In a preferred form, however, the mesh structure 412 is formed from Nitinol or similar shape memory material, which has, for example, been polished and/or heat treated. In a free-stress state, e.g., the austenitic phase, the mesh elements 420 preferably define a "stretched" condition, i.e., expand about the periphery of the mesh structure 412 such that the mesh structure 412 is biased to assume an enlarged size, e.g., substantially similar to the cross-section of a vessel within which the stent 410 is to be implanted. The mesh elements 420 may adopt an "unstretched" configuration, i.e., may be compressed about the periphery of the mesh structure 412, such that the mesh structure 412 adopts a substantially reduced size. This may be achieved by transforming the Nitinol material of the mesh structure 412 to a martensitic phase, for example, upon cooling after heat treatment. The stent 410 may then be rolled and/or collapsed to a reduced delivery profile for attachment to a stent-graft, such as those described herein.

When the stent 410 is implanted within a blood vessel, the mesh structure 412 may stretch or return to its stress-free state, e.g., the austenitic phase, and expand to engage the vessel wall. If radial pressure is applied to the stent 410 by the vessel, the mesh elements 420 may be compressed about the periphery, thereby allowing the stent 410 to recoil and substantially eliminate the likelihood of the stent 410 buckling, as may occur when a conventional coiled-sheet stent is subjected to substantial radially compressive forces.

Figure 10A:
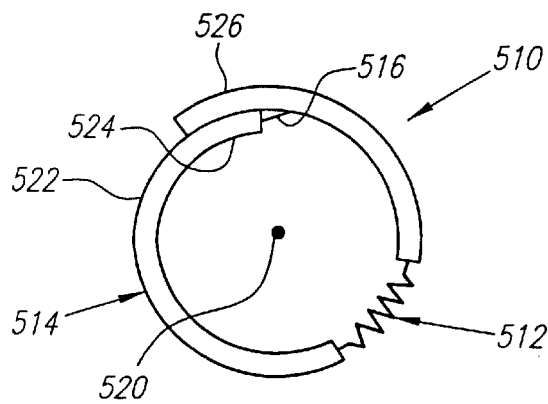
FIGS. 10A and 10B are end and side views, respectively, of a stent with anti-buckling segment.
Figure 10B:
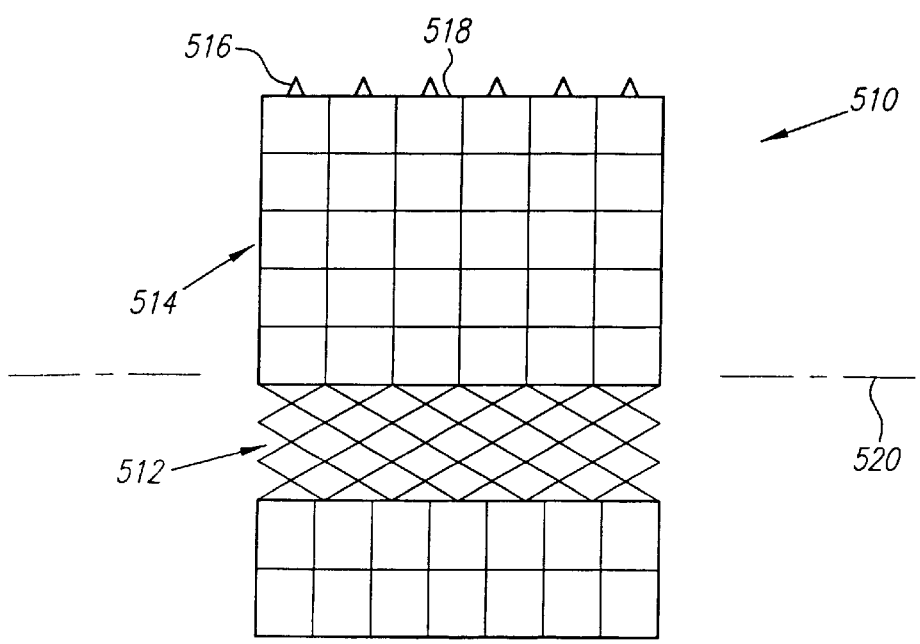

Turning to FIGS. 10A and 10B, another embodiment of a coiled-sheet stent 510 is shown that has a stretchable anti-buckling segment 512 formed from a mesh structure that is attached to a coiled-sheet portion 514. The coiled-sheet portion 514 includes teeth 516 along a side edge 518 and may be rolled or coiled to define overlapping inner and outer longitudinal sections 524, 526, a longitudinal axis 520 and a periphery 522 such that the anti-buckling segment 512 extends axially, i.e., substantially parallel to the longitudinal axis 520. Similar to the previous embodiment, the anti-buckling segment 512 may be formed from Nitinol, which may be heat treated and stretched, and then cooled and unstretched. The axially oriented anti-buckling segment 512 facilitates the entire stent 510 recoiling when subjected to radially compressive forces by providing mesh elements 524 which may be compressed about the periphery 522, as described above. Thus, the stent 510 may combine the benefits of both a coiled-sheet stent, which is generally incompressible about its periphery, and a stretchable stent structure.

Figure 11A:
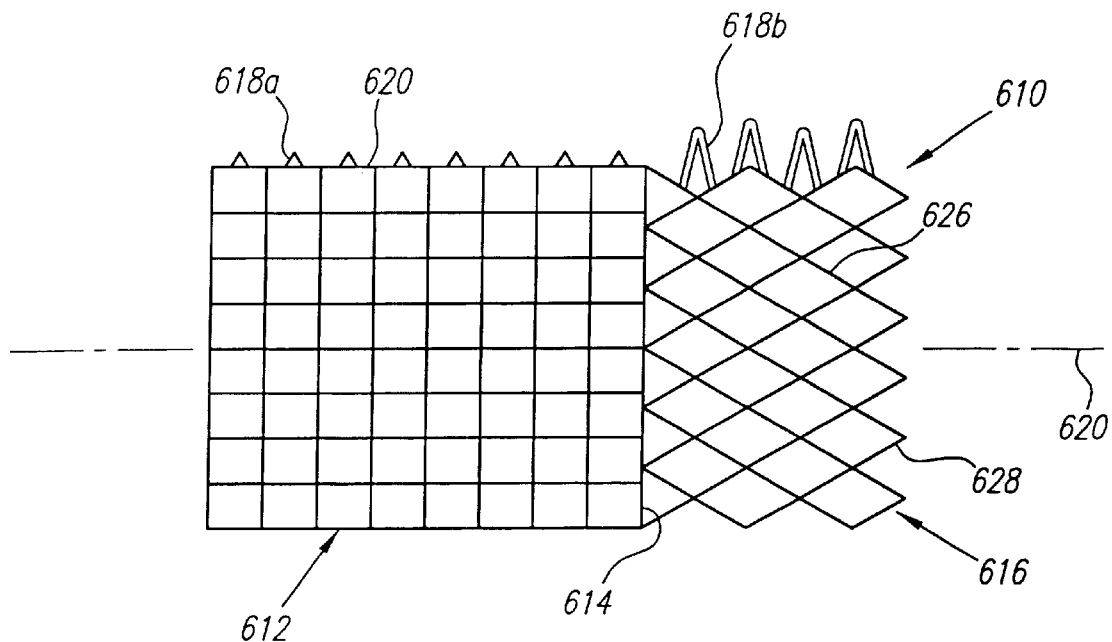
FIGS. 11A and 11B are side and perspective views, respectively, of a stent with stretchable ends.
Figure 11B:
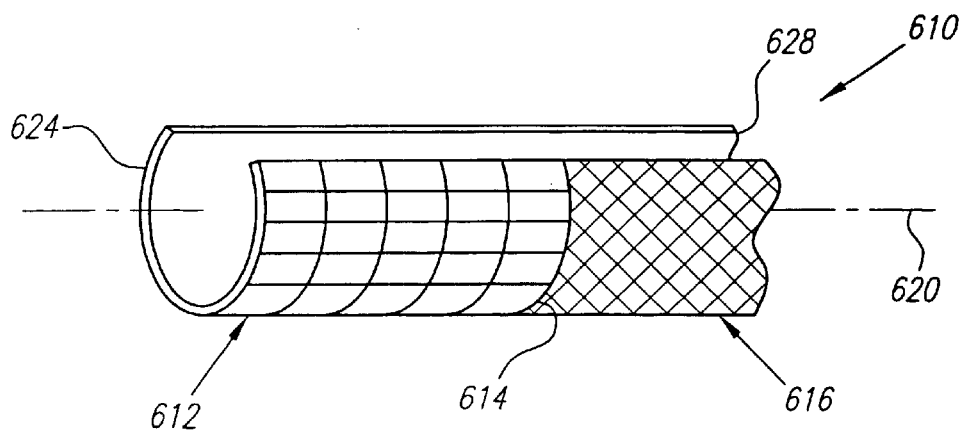

Turning to FIGS. 11A and 11B, another embodiment of a stent 610 is shown that includes an anti-buckling segment or "crowning end" 616 on one end 614 of a coiled-sheet portion 612. The coiled-sheet portion 612 and anti-buckling segment 616 include teeth 618a, 618b along a side edge 620 thereof, and may be rolled to define a longitudinal axis 622 and a perimeter 624. The anti-buckling segment 616 is preferably polished, heat treated into a desired shape, cooled and unstretched, and then coiled to its collapsed and rolled delivery profile. After being implanted, mesh elements 626 in the anti-buckling segment 616 may be compressed when the stent 610 is subjected to radially compressive forces, similar to the embodiments described above, thereby allowing the ends of the stent 610 to become tapered. Alternatively, the end 628 of the anti-buckling segment 616 may be flared outward (not shown) to thereby partially recoil under radially compressive forces such that the stent adopts a substantially uniform size upon implantation within a blood vessel.

The coiled-sheet stents 16, 18 may also include outwardly-oriented hooks or barbs (not shown) for enhancing anchoring of the stent-graft 10 within a body passage. Pro-thrombotic material (not shown) may be provided on the exterior surfaces of the coiled-sheet stents 16, 18, or alternatively on the ends 20, 22 of the tubular graft 12, to enhance sealing against the wall of the body passage. Additional information on coiled sheet stents appropriate for use with a stent-graft in accordance with the present invention may be found in U.S. Pat. Nos. 4,577,631 issued Mar. 25, 1986 in the name of Kreamer, 5,007,926 issued Apr. 16, 1991 in the name of Derbyshire, 5,158,548 issued Oct. 28, 1992 in the name of Lau et al., Re 34,327 reissued Jul. 27, 1993 in the name of Kreamer, 5,423,885 issued Jun. 13, 1995 in the name of Williams, 5,441,515 issued Aug. 15, 1995 in the name of Khosravi et al., and 5,443,500 issued Aug. 22, 1995 in the name of Sigwart. The disclosures of these references and any others cited therein are expressly incorporated herein by reference.

Figure 3A:
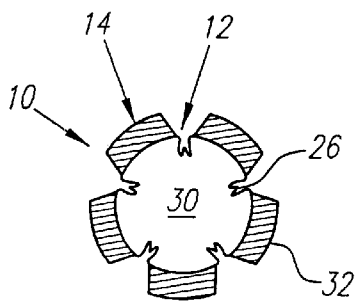
FIGS. 3A and 3B are cross-sections of the stent-graft of FIG. 1, taken along line 3—3, and showing the stent-graft in contracted and enlarged conditions, respectively.
Figure 3B:
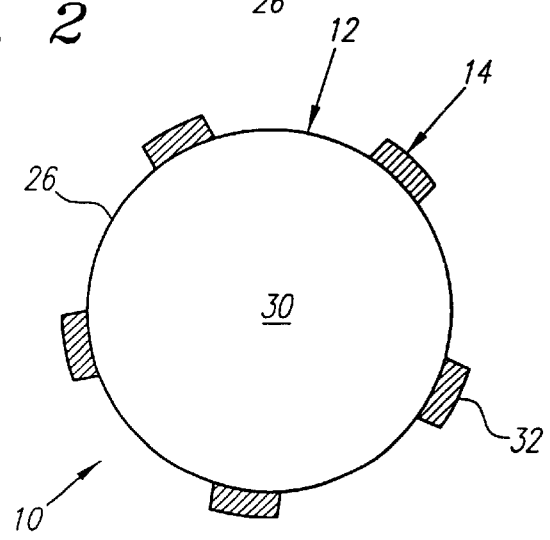

Turning to FIGS. 3A and 3B, the stent-graft 10 may be radially compressible from an enlarged condition, shown in FIG. 3B, to a contracted condition, shown in FIG. 3A. In a preferred form, the exo-skeleton 14 may be resiliently biased to assume the enlarged condition, but may be constrained in the contracted condition to facilitate introduction of the stent-graft 10 into a patient's vasculature.

For example, the stent-graft 10 may be constrained in the contracted condition, and percutaneously introduced into a blood vessel (not shown). The stent-graft 10 may be advanced to a target treatment site, e.g., within the aorta or other blood vessel (not shown), and deployed, with the exo-skeleton 14 automatically expanding to the enlarged condition. The coiled-sheet stents 16, 18 may then be expanded to a desired size to substantially engage and anchor the ends 20, 22 of the tubular graft 12 in place proximate the treatment site. Alternatively, if the coiled-sheet stents 16, 18 are provided as separate components (not shown), they may be subsequently deployed and expanded to anchor the ends 20, 22 of the previously deployed tubular graft 12.

The exo-skeleton 14 may be retained in the contracted condition simply by applying a radial compressive force to the stent-graft 10 and constraining the stent-graft 10, for example, within a sheath. Alternatively, if the exo-skeleton 14 is formed from Nitinol, the martensitic properties of the Nitinol may be used to substantially retain the stent-graft 10 in the contracted condition after being radially compressed. The "zigzag" configuration of the serpentine elements 32 of the exo-skeleton 14 may facilitate substantially uniform radial compression of the stent-graft 10 when it is subjected to radially compressive forces, as shown in FIG. 3A, thereby minimizing the risk of localized stress in the exo-skeleton 14 and/or the tubular graft 12.

When the exo-skeleton 14 automatically assumes the enlarged condition, the serpentine elements 32 preferably substantially expand and support the peripheral wall 26 of the tubular graft 12, thereby maintaining the lumen 30 substantially open and unobstructed, as may be seen in FIG. 3B, for example, to facilitate blood flow through the treatment site being repaired. In an alternative form, the exo-skeleton 14 may be initially formed in the contracted condition, but may be plastically deformable to the enlarged condition, for example, using a balloon or other expandable member after the stent-graft 10 has been deployed at the treatment site, as will be appreciated by those skilled in the art.

The multi-cellular configuration provided by the plurality of serpentine elements 32 of the exo-skeleton 14 may facilitate the stent-graft 10 conforming substantially to tortuous anatomy during advancement and/or upon deployment at a treatment site. If the stent-graft 10 is subjected to substantially transverse forces, for example, when it is directed around a tightly curved region of a blood vessel, the stent-graft 10 may be easily articulated between adjacent serpentine elements 32 to conform to the shape of the blood vessel. In addition, the zigzag elements of each serpentine element 32 may be resiliently deformable, thereby further facilitating conformance with local anatomic conditions. Thus, a stent-graft 10 in accordance with the present invention may have a substantially flexible intermediate region 29 extending between substantially rigid anchoring stents 16, 18. The intermediate region 29 may allow the tubular graft 12 to conform to the anatomy of the treatment site, while the exo-skeleton 14 substantially supports the tubular graft 12 to prevent collapse or buckling.

Turning to FIG. 4, another preferred form of an exo-skeleton 114 is shown that includes one or more serpentine elements 132 attached to the peripheral wall 126 of a tubular graft 112 (in phantom) that extend substantially axially along the longitudinal axis 124 of a stent-graft 110. Each serpentine element 132 preferably defines a generally sinusoidal shape extending substantially axially along the peripheral wall 126, and includes substantially transverse peripheral elements 134, with adjacent peripheral elements 134 being connected by alternating curved elements 136 to define the generally sinusoidal shape.

In a preferred form, a plurality of serpentine elements 132 may be provided distributed substantially evenly about the periphery of the peripheral wall 126. For example, as shown in FIGS. 5A–5D, a pair of serpentine elements 132 may be attached to the peripheral wall 126 opposite one another.

Turning to FIGS. 5A–5D, a stent-graft 110 having a pair of axial serpentine elements 132a, 132b is shown being rolled from an enlarged condition to a contracted condition. The exo-skeleton 114 is preferably biased to assume the enlarged condition of FIG. 5A. Because of the spaces 133 extending substantially axially between the serpentine elements 132a, 132b, the stent-graft 110, including coiled-sheet stents (not shown) on the ends of the stent-graft 110, may be flattened, as shown in FIG. 5B. One edge of the stent-graft 110 may then be rolled, similar to a coiled-sheet stent, as shown in FIG. 5C, until the entire stent-graft 110 is fully rolled into the contracted condition, shown in FIG. 5D, thereby providing a reduced profile. The stent-graft 110 may then be retained in the contracted condition to facilitate introduction into and advancement within a patient's vasculature, until deployed at a target treatment site, whereupon the stent-graft 110 may automatically expand to its enlarged condition.

Figure 6:
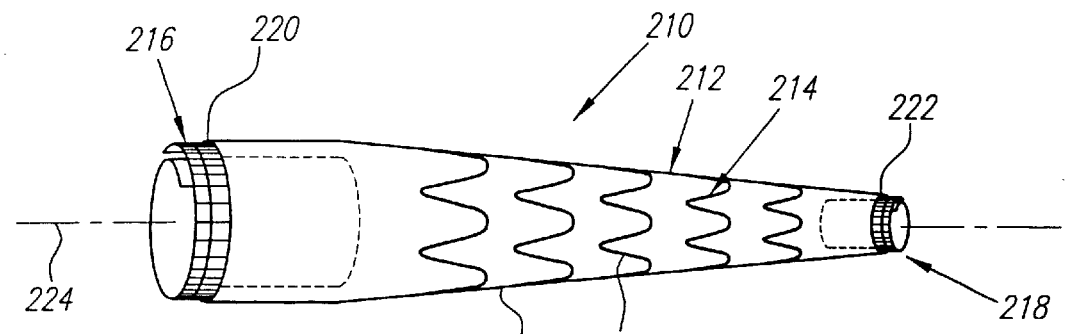
FIG. 6 is a perspective view of another embodiment of a stent-graft, having a tapered configuration.

Turning to FIG. 6, another preferred embodiment of a stent-graft 210 is shown, which has a substantially tapered configuration between its first and second ends 220, 222. Similar to the previous embodiments, the stent-graft 210 has a tubular graft 212 to which an exo-skeleton 214 is attached to provide a resilient, flexible region. Coiled-sheet stents 216, 218 are attached to the ends 220, 222 of the tubular graft 212 for anchoring the ends 220, 222 within a body passage. The second end 222 of the tubular graft 212 has a diameter that is substantially smaller than the first end 220 to conform substantially to the anatomy of a tapered blood vessel or to extend between a first larger vessel and a second smaller vessel.

Figure 8:
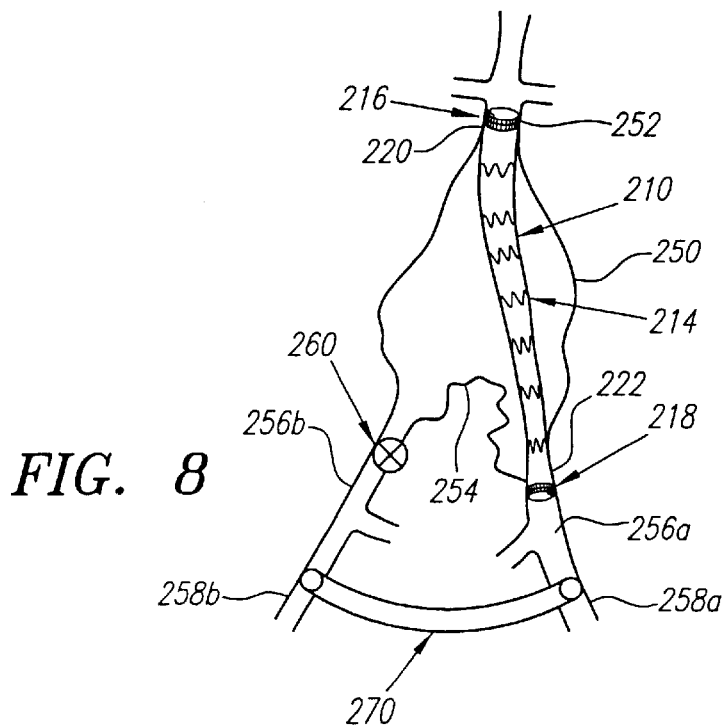
FIG. 8 is a cross-sectional view of an abdomen, showing a method for implanting a stent-graft across a bifurcation for treating an aneurysm at the bifurcation.

Turning to FIG. 8, a tapered stent-graft 210, such as that just described, may be used in a method for repairing an aortic aneurysm 250 that extends from an abdominal aorta 252 through a bifurcation 254 into the iliac arteries 256a, 256b. The stent-graft 210, in a contracted condition, may be introduced across the bifurcation 254 with the larger first end 220 oriented towards the abdominal aorta 252. For example, the stent-graft 210 may be placed on a catheter delivery device (not shown), percutaneously introduced into a peripheral artery (not shown), advanced into the ipsilateral iliac artery 256a, and through the bifurcation 254 until the first end 220 reaches an undamaged region of the abdominal aorta 252. The stent-graft 210 may be then deployed and expanded to its enlarged condition, for example, when the exo-skeleton 214 automatically expands upon deployment. Coiled-sheet stents 216, 218 on the stent-graft 210 may be expanded to substantially seal and anchor the stent-graft 210 to undamaged regions of the abdominal aorta 252 and the ipsilateral iliac artery 256a, respectively.

The contralateral iliac artery 256b may be substantially permanently occluded with a vessel occluder 260, and a femoral-to-femoral bypass graft 270 may be attached between the femoral arteries 258, or alternatively between the iliac arteries 256, to allow blood flow from the ipsilateral iliac artery 256a into the contralateral iliac artery 256b and beyond.

Figure 7:
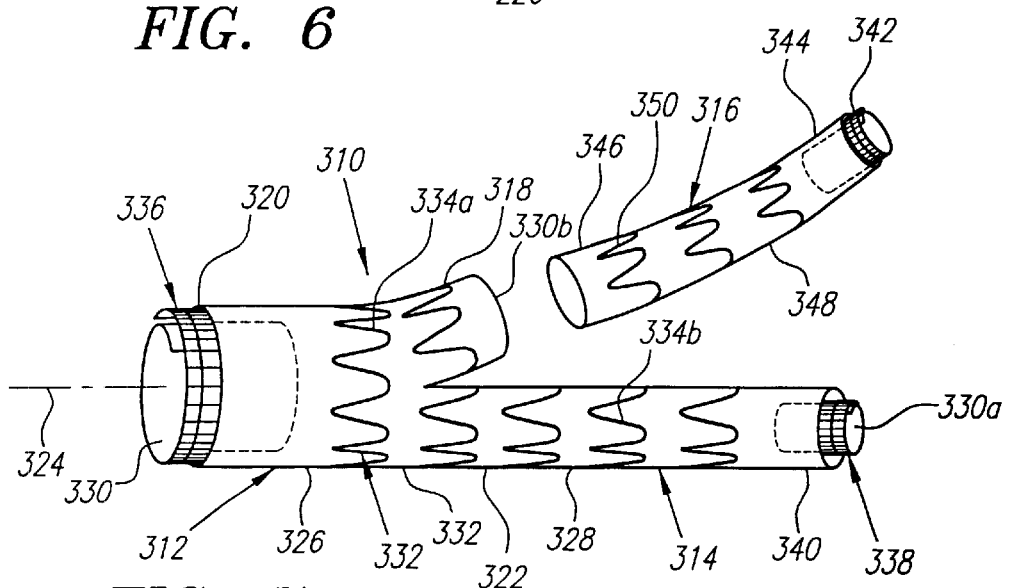
FIG. 7 is a perspective view of still another embodiment of a stent-graft, having a bifurcated main segment, an extension segment and an attachable docking limb.

Turning to FIG. 7, a stent-graft 310 for repairing a bifurcation is shown, in accordance with another aspect of the present invention. The stent-graft 310 includes a plurality of tubular segments, namely a first main segment 312, a second extension segment 314 extending from the first segment 312, and a third segment or "docking limb" 316 that is attachable to a collar 318 on the first segment 312. The first segment 312 has a first end 320 and a second bifurcated end 32 defining a longitudinal axis 224 therebetween, with the second segment 314 and the collar 318 extending adjacent one another from the second bifurcated end 322.

The first and second segments 312, 314 have first and second peripheral walls 326, 328, respectively, which may be integrally formed together, or may be provided as separate wall portions that are attached to one another. The first peripheral wall 326 defines a lumen 330 that extends from the first end 320 through the first segment 312 and is bifurcated into a first branch lumen 330a defined by the second peripheral wall 328 and a second branch lumen 330b at least partially defined by the collar 330b.

An exo-skeleton 332 is attached to at least one of the first and second peripheral walls 326, 328 and/or the collar 318, which includes a plurality of serpentine elements 334, similar to the serpentine elements previously described herein. Preferably, a first set of serpentine elements 334a are attached to the first peripheral wall 326 to support the first segment 312, and a second set of serpentine elements 334b are attached to the second peripheral wall 328 to support the second segment 314. The serpentine elements 334 may be individually attached to the respective peripheral walls 326, 328 and/or adjacent serpentine elements may be connected to one another by one or more connector elements (not shown), as described above.

A first coiled-sheet stent 336 is attached to the first end 320 for substantially anchoring and/or sealing the first end 320 within a body passage. Similarly, a second coiled-sheet stent 338 is attached to a distal end 340 of the second segment 314.

The docking limb 316 has a third peripheral wall 348 to which one or more serpentine elements 350 may be attached, thereby further defining the exo-skeleton 332 of the stent-graft 310. A third coiled-sheet stent 342 may be attached to a first or distal end 344 of the docking limb 316. A second or proximal end 346 of the docking limb 316 is attachable to the collar 318 on the first segment 312, for example, by a lap connection, or alternatively using another coiled-sheet stent (not shown).

The exo-skeleton 332 may be directed between a contracted condition for facilitating introduction within a body passage and an enlarged condition for deployment within the body passage, similar to the stent-grafts previously described herein. For example, each serpentine element 334a, 334b, 350 may be radially compressible to its contracted condition and biased to assume its enlarged condition.

In a preferred form, the first end 320 of the first segment 312 has a size in its enlarged condition that corresponds substantially to the diameter of an undamaged region of an abdominal aorta. The distal ends 340, 344 of the second segment 314 and the docking limb 316 have sizes in their enlarged conditions that are substantially smaller than the size of the first segment 312, preferably corresponding substantially to the diameter of an undamaged region of an iliac artery.

The first and second segments 312, 314 may be radially compressed into their contracted conditions and directed within a patient's vasculature to a bifurcated treatment site, such as a site of an aneurysm at the aorto-iliac bifurcation (not shown), similar to that shown in FIG. 8. The first end 320 may be aligned with an undiseased region of the abdominal aorta proximate the aneurysm, with the second segment 314 extending into a first iliac artery and the collar 318 oriented towards a second iliac artery. The first and second segments 312, 314 may be deployed and expanded to their enlarged conditions, and the first and second coiled-sheet stents 336, 338 expanded to substantially engage the walls of the undiseased abdominal aorta and first iliac artery, respectively.

The docking limb 316, in its contracted condition, may be advanced into the second iliac artery, and the proximal end 346 aligned with the collar 318. The docking limb 316 may then be deployed and expanded to its enlarged condition such that the proximal end 346 substantially engages the collar 318. The third coiled-sheet stent 342 may be expanded to substantially seal and engage an undiseased region of the second iliac artery.

Thus, the damaged region of the aorto-iliac bifurcation may be completely bypassed using a stent-graft 310 in accordance with the present invention. The flexible exoskeleton 332 may allow the stent-graft 310 to conform substantially to the anatomy at the bifurcated treatment site, while supporting the tubular graft segments 312, 314, 316 to provide a substantially open and unobstructed lumen to accommodate the flow of blood therethrough. The coiled-sheet stents 336, 338, 342 may substantially anchor the respective ends 320, 340, 344 of the stent-graft 310 and/or substantially seal the stent-graft 310 to the walls of the vessels.

Figure 12:
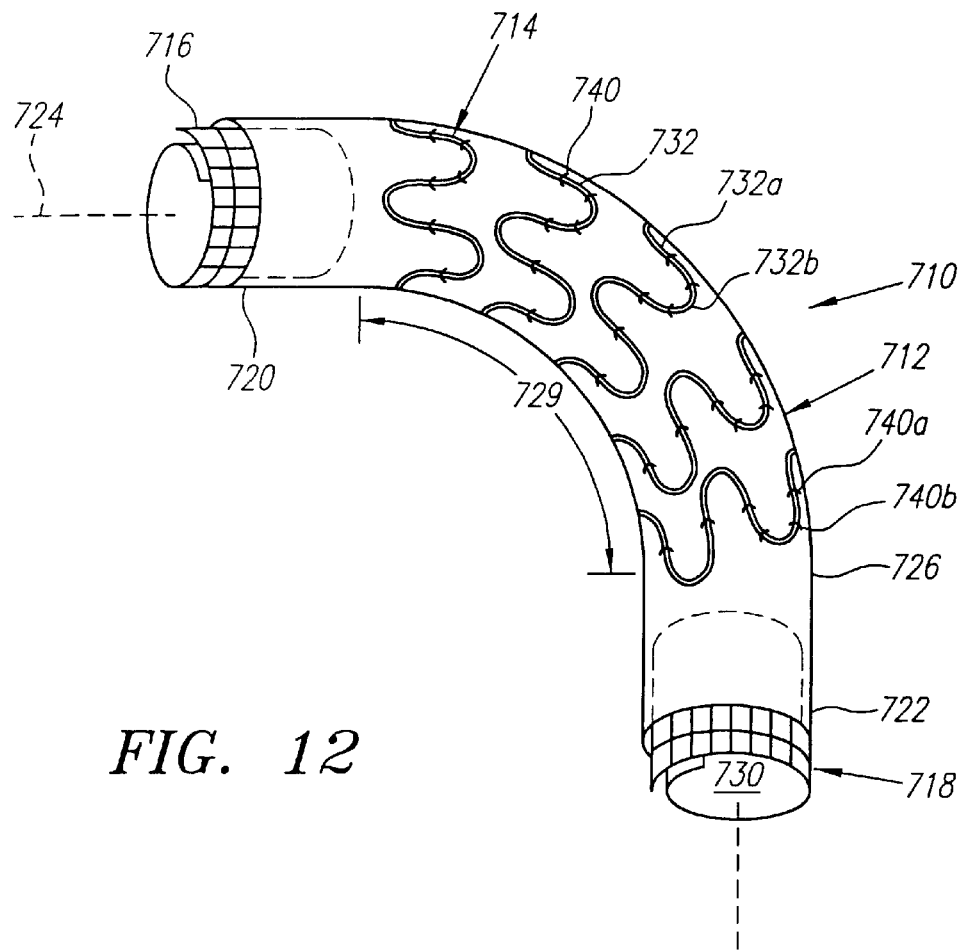
FIG. 12 is a perspective view of a stent-graft with slidable exo-skeleton in accordance with the present invention.

Turning to FIG. 12, a preferred embodiment of a stent-graft 710 is shown, in accordance with still another aspect of the present invention. Similar to the previous embodiments, the stent-graft 710 generally includes a tubular graft 712, an exo-skeleton 714 attached to the tubular graft 712, and a pair of stents 716, 718 attached to ends 720, 722 of the tubular graft 712. The tubular graft 712 has a peripheral wall 726 defining a circumference or other periphery and has a lumen 730 therein extending axially between the first and second ends 720, 722 of the graft 712.

The stents 716, 718 are preferably coiled-sheet stents, similar to those described previously, that are attached to the first and second ends 720, 722 such that they extend partially from the respective ends 720, 722. Alternatively, the stents 716, 718 may be separately deployable after the tubular graft 712 has been delivered to a target location to anchor the ends 720, 722 of the tubular graft 712 to the wall of the body lumen. In a further alternative, the exo-skeleton 714 may sufficiently support the tubular graft 712 that the stents 716, 718 may not be necessary, although their use is preferred to prevent migration or leaking.

The exo-skeleton 714 includes a plurality of support elements 732 attached to the tubular graft 712, each support element 732 having a generally annular or ring shape extending generally circumferentially or otherwise peripherally around the tubular graft 712 and including generally axial segments 732a and generally peripheral segments 732b. Preferably, each support element 732 has a generally serpentine shape, such that the generally axial segments 732a are connected by alternating generally peripheral segments 732b that are curved to provide a zigzag or sinusoidal shape, similar to the embodiments previously described. The support elements 732 are preferably independently attached to the tubular graft 712, although alternatively they be connected to one another by one or more connector elements, similar to the embodiments described above.

The support elements 732 of the exo-skeleton 714 are attached to the tubular graft 712 by fasteners 740, such as sutures, wires, staples, and the like. Preferably, a set of first fasteners 740a slidably secures axial segments 732a, such that the axial segments 732a may slide within respective first fasteners 740a, and consequently may slide with respect to respective first wall regions to which the first fasteners 740a are secured. For example, as shown in FIG. 12, each axial segment 732a of each support element 732 may be engaged by a first fastener 740a such that each axial segment 732a may slide axially with respect to the respective first fastener 740a, which may facilitate articulation of the tubular graft 712 between adjacent support elements 732, as explained further below.

Preferably, the first fasteners 740a fit substantially snugly around the secured respective axial segments 732a, i.e., the first fasteners 740a have a width along the circumference of the tubular graft 712 that is similar to the thickness of the axial segments 732a, thereby preventing substantial movement of the axial segments 732a circumferentially along the tubular graft 712, but still allowing axial movement. Alternatively, the fasteners 740a may have a width that is substantially larger than the thickness of the axial segments 732a, thereby providing a degree of circumferential movement if desired.

In addition, a set of second fasteners 740b also secures portions of the support elements 732 to the wall 726 of the graft 712. Preferably, the second fasteners 740b substantially anchor, i.e., nonslidably secure, at least one peripheral segment 740b of each support element 732 to respective second wall regions of the tubular graft 712. For example, in the preferred form shown in FIG. 12, a second fastener 740b may anchor the peripheral segment 732b of each support element 732 that are aligned axially with one another to generally position the support elements 832 evenly along the length of a flexible region 729 of the tubular graft 712. The other peripheral segments 740b may be free to move axially with respect to the tubular graft 712 as the axial segments 832a slide within their respective first fasteners 840a.

In a preferred form, each of the first and second fasteners 740a, 740b is a single suture loop or a plurality of suture loops which may be sewn into the tubular graft 712 and around the respective axial or peripheral segments 732a, 732b of the support elements 732. Preferably, the sutures are applied in a generally circumferential sequence to facilitate manufacturing, e.g., such that a single thread may be used to provide a plurality of first and/or second fasteners 740a, 740b.

Figure 13:
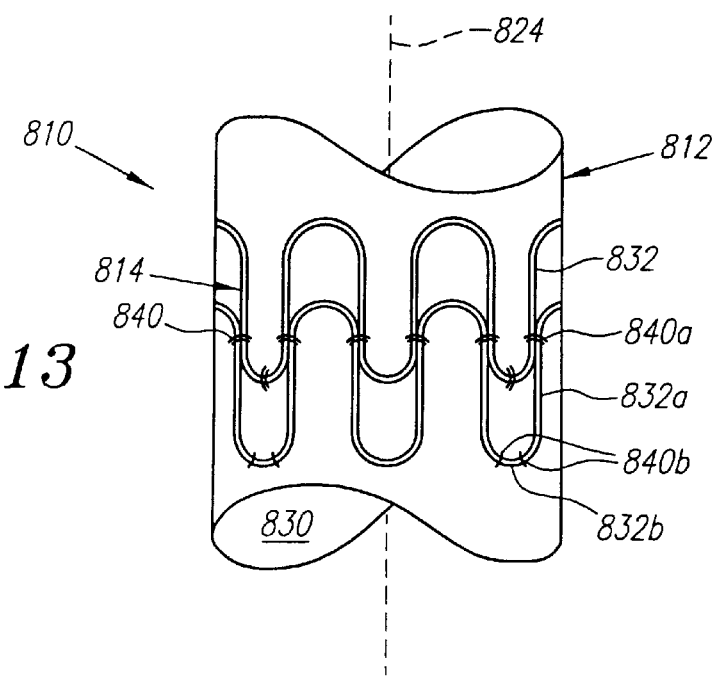
FIG. 13 shows an alternative embodiment of the flexible intermediate region of a stent-graft with slidable exo-skeleton.

Turning to FIG. 13, an alternative embodiment of a stent-graft 810 with a slidable exo-skeleton 814 is shown. Unlike the previous embodiment, each first fastener 840a slidably secures two axial segments 832a of adjacent support members 832, thereby fixing the relative circumferential position of the secured axial segments 832a, but allowing them to slide axially with respect to the respective first fastener 840a and each other. In addition, second fasteners 840b are used to anchor every other peripheral segment 832b of each support element 832, thereby further fixing the axial position of the support elements 832 along the tubular graft 812, while allowing some axial sliding of the support elements 832.

Accordingly, a slidable exo-skeleton in accordance with the present invention may facilitate articulation of a stent-graft during use. This may be particularly important when the stent-graft is directed through and/or implanted within a tortuous body passage, such as the bifurcation where the iliac arteries extend from the abdominal aorta (not shown). As the stent-graft is bent transversely, i.e., into a curved shape, the support elements of the exo-skeleton may retain their general position along the length of the tubular graft, but may partially slide with respect to the tubular graft and with respect to one another. More specifically, the axial segments of the support elements along the inside radius of the curve will generally slide axially closer to one another, while the axial segments along the outside radius of the curve will generally slide axially away from one another.

Because the support elements are secured to the tubular graft by the first and second fasteners, the support elements continue to support the wall of the tubular graft, even as the stent-graft is bent. Because the support elements may slide, they substantially minimize the creation of large folds of graft material, particularly within the inside radius of the turn. Thus, the slidable exo-skeleton may reduce the risk of kinking and therefore hold the lumen of the tubular graft substantially open. In addition, slidable support elements may substantially reduce the risk of buckling or pinching of graft material between adjacent support elements.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A stent-graft, comprising:
   a tubular graft having a wall generally defining a circumference and having a lumen therein, the lumen extending axially between first and second open ends of the tubular graft;
   an exo-skeleton for supporting the wall of the tubular graft, the exo-skeleton comprising a plurality of generally annular-shaped support elements distributed axially along the wall of the tubular graft, each support element including generally axial segments and generally circumferential segments;
   a plurality of first fasteners for attaching the plurality of support elements to the wall of the tubular graft, at least one generally axial segment being slidably engaged by each first fastener; and
   a plurality of second fasteners for attaching the plurality of support elements to the wall of the tubular graft, each second fastener substantially anchoring a segment of the respective support element to the wall of the tubular graft.

2. The stent-graft of claim 1, wherein each of said support elements has one or more second fasteners attaching at least one segment of a support element to the wall of the tubular graft.

3. The stent-graft of claim 1, wherein each of said support elements has one or more second fasteners attaching one segment of a support element to the wall of the tubular graft.

4. The stent-graft of claim 2, wherein said plurality of second fasteners are substantially aligned axially with one another.

5. The stent-graft of claim 4, wherein said support elements are generally positioned evenly along the length of a flexible region of the tubular graft.

6. The stent-graft of claim 1, wherein said plurality of first fasteners comprise a suture loop sewn into the tubular graft and around a portion of a support element.

7. The stent-graft of claim 1, wherein said plurality of second fasteners comprise a suture loop sewn into the tubular graft and around a portion of a support element.

8. The stent-graft of claim 1, wherein the plurality of first fasteners is selected from the group consisting of sutures, staples, and wires.

9. The stent-graft of claim 1, wherein the plurality of second fasteners is selected from the group consisting of sutures, staples, and wires.

10. The stent-graft of claim 1, further comprising a stent on the first open end for substantially anchoring the first open end within a body passage.

11. The stent-graft of claim 10, wherein the stent on the first open end comprises a coiled-sheet stent.

12. The stent-graft of claim 10, wherein the stent includes external outwardly oriented hooks for engaging a wall of a body passage.

13. The stent-graft of claim 10, further comprising prothrombotic material on an exterior surface of at least the stent, or one of the first and second open ends of the tubular graft.

14. The stent-graft of claim 1, further comprising a plurality of support elements distributed axially along the tubular graft for providing articulation of the tubular graft between adjacent support elements.

15. The stent-graft of claim 1, wherein the support elements are directable between a contracted condition for facilitating introduction within a body passage and an enlarged condition for deployment within the body passage, the support elements substantially supporting the tubular graft to hold the lumen of the tubular graft substantially open in the enlarged condition.

16. The stent-graft of claim 15, wherein the support elements are radially compressible to the contracted condition and biased to assume the enlarged condition.

17. The stent-graft of claim 1, wherein the tubular graft comprises a polymeric material.

18. The stent-graft of claim 17, wherein the polymeric material is selected from the group consisting of polyester, polytetrafluoroethylene, dacron, teflon, and polyurethane.

19. The stent-graft of claim 1, wherein each support element comprises a generally serpentine shaped member.

20. The stent-graft of claim 19, wherein each serpentine shaped member comprises a wire formed into a generally curved zigzag shape.

21. The stent-graft of claim 1, wherein the first open end of the tubular graft has a cross-section that is substantially smaller than a cross-section of the second end of the tubular graft.

22. The stent-graft of claim 1, wherein the support elements are attached to an exterior surface of the tubular graft.

23. The stent-graft of claim 1, wherein at least one of said first fasteners slidably engages one generally axial segment of each of two adjacent support elements.

* * * * *